(12) United States Patent
Martens, III et al.

(10) Patent No.: US 6,450,419 B1
(45) Date of Patent: Sep. 17, 2002

(54) SELF CONTAINED LIQUID ATOMIZER ASSEMBLY

(75) Inventors: Edward J. Martens, III, Racine, WI (US); George A. Clark, Lewis Center, OH (US); Thomas A. Helf, New Berlin, WI (US); Eric R. Navin, Delaware, OH (US); David J. Schram, Waterford, WI (US); David A. Tomkins, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 76 days.

(21) Appl. No.: 09/699,106

(22) Filed: Oct. 27, 2000

(51) Int. Cl.[7] .................................................. B05B 1/08
(52) U.S. Cl. ................................. 239/102.1; 239/102.2
(58) Field of Search .......................... 239/102.1, 102.2, 239/44–47, 35, 55; 215/341, 343, 346, 45; 220/304, 795, 300, 301, 293, 378

(56) References Cited

U.S. PATENT DOCUMENTS

| 4,119,096 A | 10/1978 | Drews |
| 4,294,407 A | 10/1981 | Reichl et al. |
| 4,300,546 A | 11/1981 | Kruber |
| 4,301,093 A | 11/1981 | Eck |
| 4,334,531 A | 6/1982 | Reichl et al. |
| 4,479,609 A | 10/1984 | Maeda et al. |
| 4,790,479 A | 12/1988 | Matsumoto et al. |
| 4,793,339 A | 12/1988 | Matsumoto et al. |
| 4,877,989 A | 10/1989 | Drews et al. |
| 5,217,165 A | 6/1993 | Takahashi et al. |
| 5,312,281 A | 5/1994 | Takahashi et al. |
| 5,419,879 A | 5/1995 | Vlahakis et al. |
| 5,529,055 A | 6/1996 | Gueret |
| 5,657,926 A | 8/1997 | Toda |
| 5,803,362 A | 9/1998 | Fraccaroll |
| 5,921,232 A | 7/1999 | Yokoi et al. |

Primary Examiner—Lisa A. Douglas

(57) ABSTRACT

A liquid atomizer is constructed with a hollow shell-like top cover and a unitary molded main support which snaps into place inside the top cover and divides it into upper and lower regions. The main support includes formations for mounting, on its upper side, a printed circuit board assembly including an electrical oscillator, as well as a piezoelectric actuator and orifice plate pump assembly. The main support also includes formations for removably mounting, on its lower side, a battery and a liquid reservoir. An openable bottom cover closes the bottom of the device and allows access to the battery and to the liquid reservoir for replacement of these elements.

31 Claims, 3 Drawing Sheets

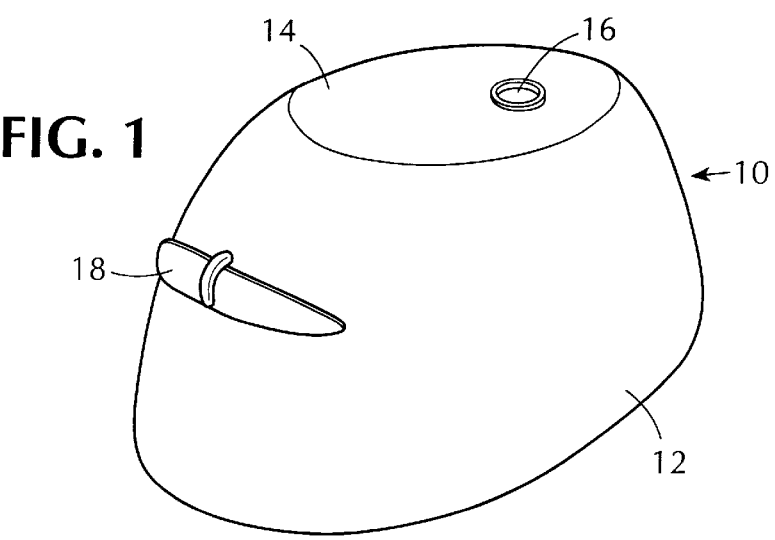
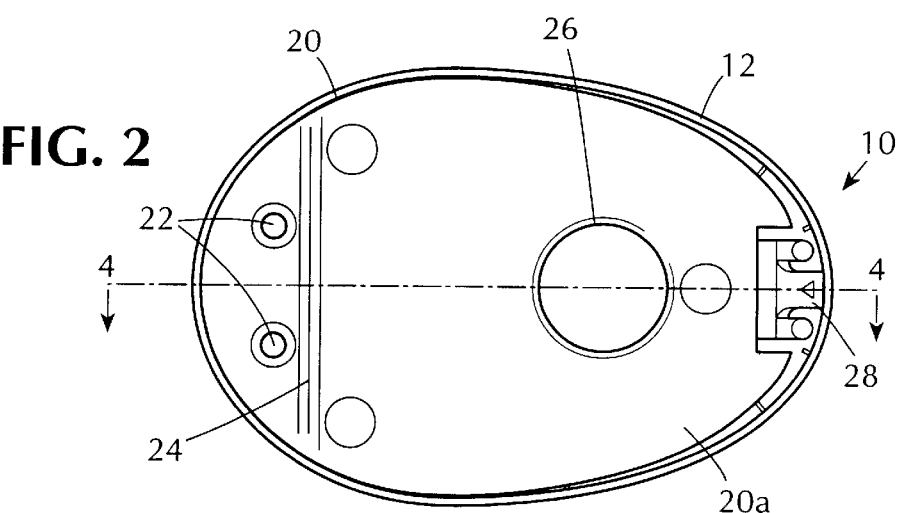
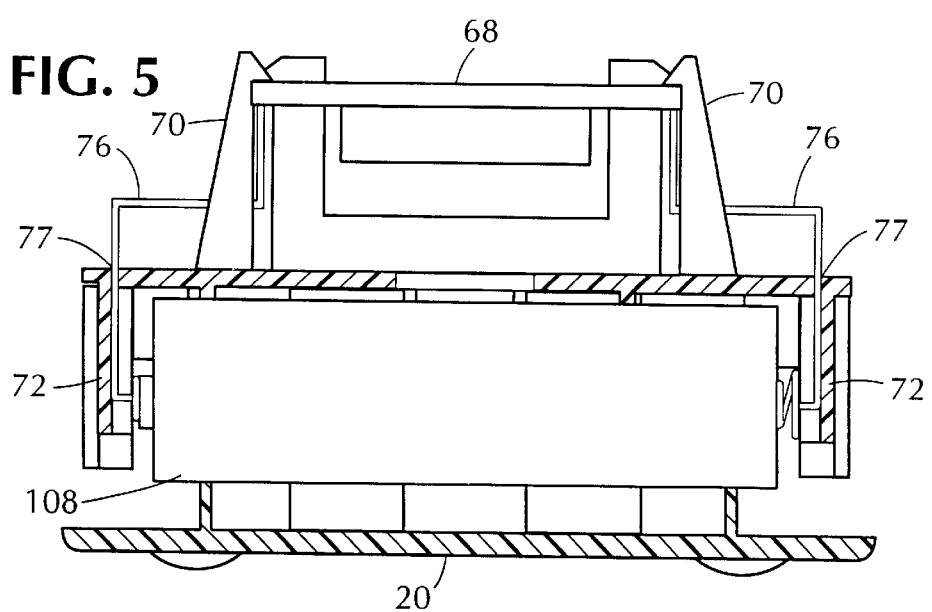

SELF CONTAINED LIQUID ATOMIZER ASSEMBLY

BACKGROUND OF THE INVENTION

1. Field of the Invention

This invention relates to liquid atomizers and more particularly it concerns a self contained battery powered atomizer which uses a vibrated orifice plate to produce and eject aerosolized particles from a liquid supply.

2. Description of the Related Art

Self contained battery powered liquid atomizing devices are well known and are described, for example, in U.S. Pat. Nos. 4,294,407; 4,300,546; 4,334,531; 4,479,609; 4,793,339, 4,877,989; 5,529,055 and 5,803,362. These known devices are generally expensive to manufacture and are impractical for use in household applications such as dispensing of fragrances, insecticides and the like, while retaining the precision necessary for such operations.

SUMMARY OF THE INVENTION

The present invention makes possible a reliable yet inexpensive and easily manufactured and assembled, battery powered liquid atomizing device having a conveniently replaceable liquid reservoir which can be positioned in the device with the precision necessary for proper supply of liquid to the atomizing mechanism.

According to one aspect of the invention there is provided in a liquid atomizer device, a hollow shell-like outer housing or top cover formed with an upper atomized liquid ejection opening and a generally horizontal integrally molded chassis or support inside the outer housing and which divides the interior of the top cover into upper and lower regions. The support is formed with a passageway which communicates between the upper and lower regions in the top cover. The support is also formed, on its upper and lower sides, respectively, with upwardly and a downwardly facing locating surfaces next to the passageway. The upwardly facing locating surface locates a vibratory orifice plate on the upper side of the support and the downwardly facing locating surface locates a replaceable liquid reservoir on the lower side of the support. The support is further formed with an upwardly facing camming surface which is located below the downwardly facing surface and this camming surface holds a liquid reservoir up against the downwardly facing locating surfaces for precise positioning of a liquid reservoir relative to an orifice plate mounted on said upwardly facing locating surface. Because the upwardly and downwardly facing locating surfaces are formed on the same support, the orifice plate, which locates on the upwardly facing surface, and the liquid reservoir, which locates on the downwardly facing surface, can be positioned precisely relative to each other, even when a replacement liquid reservoir is inserted into the dispenser. As a result, a wick, which extends out of the reservoir, delivers the liquid to the orifice plate without appreciably damping its vibrations. Thus, liquid is delivered to the orifice plate without any interference with vibration of the plate.

According to a second aspect of the invention, there is provided a liquid atomizer device which comprises a hollow shell-like outer housing or top cover formed with an upper atomized liquid ejection opening and a generally horizontal chassis or support which divides the interior of the top cover into upper and lower regions. The support is formed with a passageway communicating between the upper and lower regions; and it is also formed, on its upper and lower sides, respectively, with mounting formations for mounting an orifice plate in an upper region of the passageway and for removably mounting liquid reservoir in a lower region of the passageway. The support is also formed on its upper side with circuit mounting elements for mounting an electrical drive circuit which causes an orifice plate to vibrate. In addition, the support is formed on its lower side with battery mounting elements. This arrangement provides easy access for replacement of either or both the battery and the liquid reservoir without disturbing the vibratory orifice plate or the drive circuit.

According to a further aspect of the invention, there is provided a novel retainer assembly for a piezoelectric atomizing pump of the type which comprises an annular piezoelectric element having a center opening and an orifice plate fixed to the element and extending across its opening. This novel retainer assembly comprises a vertically extending generally cylindrical wall within which a piezoelectric atomizing pump assembly may fit. The tubular support is also formed with an inwardly extending shelf for supporting the piezoelectric pump assembly. A pump assembly retainer is also provided. This retainer has a laterally extending annular wall which rests on the upper end of the cylindrical wall above the shelf and is removably secured to the tubular support. A plurality of resilient retainer elements extend downwardly from an inner edge of the annular wall and inside the tubular support to press on and hold the piezoelectric pump assembly which rests on the shelf. This allows the piezoelectric pump assembly to be precisely positioned on the shelf; and yet, because of the resilient retainer elements, any variations in the size of the tubular support, the pump assembly retainer or the piezoelectric pump assembly are accommodated by the flexing of the resilient retainer elements.

In a still further aspect, the present invention provides an easily assemblable, self contained liquid atomizer assembly which comprises a hollow molded outer shell or top cover having support projections which extend inwardly from an inner surface thereof and retainer formations which are located below the support formations. The top cover is also formed with an upper atomized liquid ejection opening. There is also provided a unitary molded internal chassis or support having a flange-like surface which can be snapped into place inside the top cover to rest against the support projections inside the top cover. The internal support has a passage which is aligned with the ejection opening in the outer shell when the support is snapped into place. The upper side of the internal support is formed with upwardly facing support surfaces on which a printed circuit board may rest and on which a piezoelectric pump assembly, positioned over the passage, may rest. The upper side of the support is also provided with snap elements which permit the printed circuit board and the pump assembly to be snapped into and held in place on the upper side of the internal support. The lower side of the internal support is formed with releasable retainer elements for releasably holding a liquid reservoir under the passage and for releasably holding a battery adjacent to the reservoir. Finally, the internal support is formed with openings to accommodate wires which extend from a battery held under the support to a printed circuit board held above the support and which extend from the printed circuit board to the piezoelectric pump assembly held on the upper side of the support.

BRIEF DESCRIPTION OF THE DRAWINGS

FIG. 1 is a perspective view of the outside of an atomizer assembly which embodies the present invention;

FIG. 2 is a bottom plan view of the underside of the atomizer assembly of FIG. 1;

FIG. 5 is an elevational section view taken along line 5—5 of FIG. 4.

DETAILED DESCRIPTION OF THE PREFERRED EMBODIMENT

Figure 3:
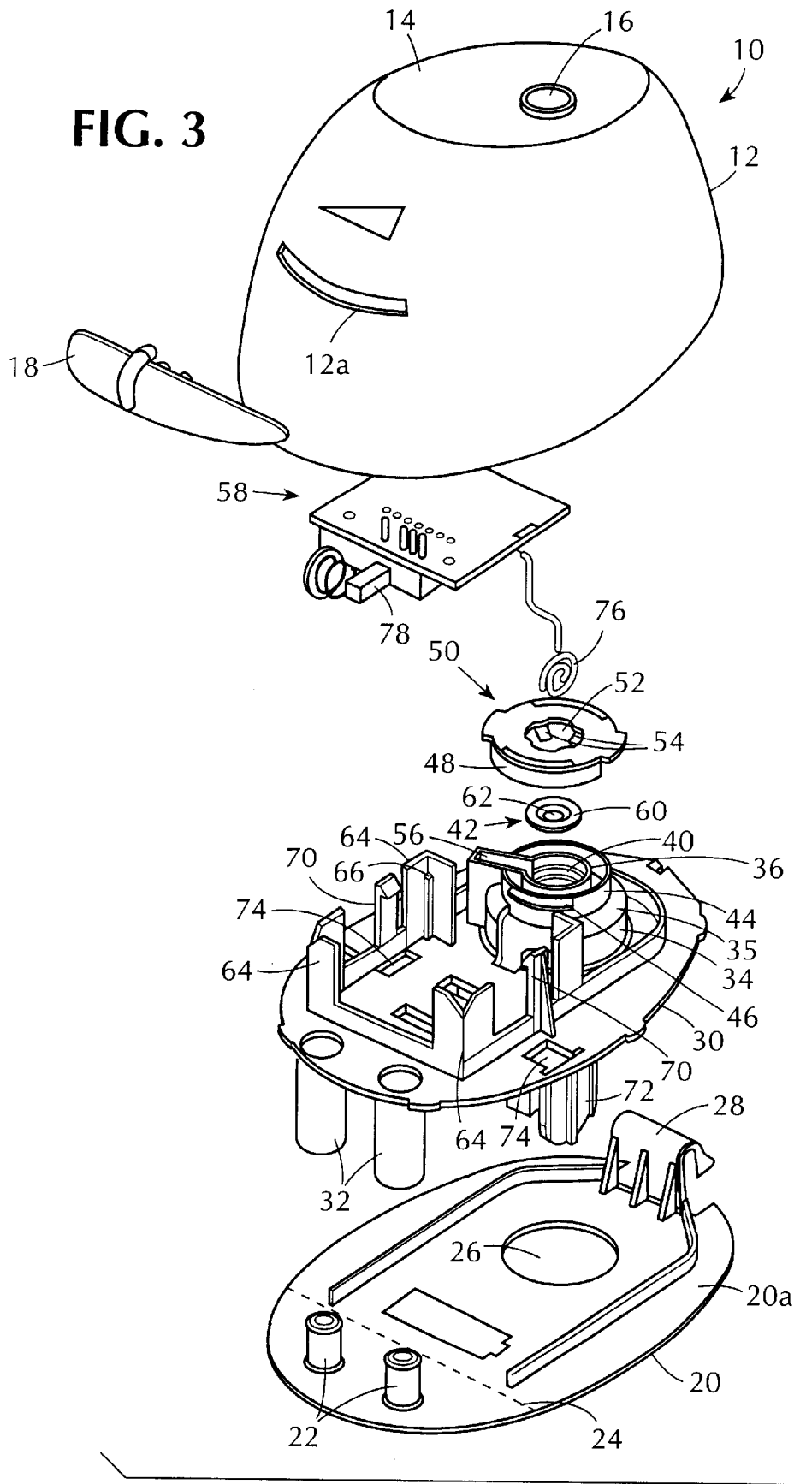
FIG. 3 is an exploded perspective view showing the internal construction of the atomizer assembly of FIGS. 1 and 2.

As shown in FIG. 1 an atomizing device 10 according to the present invention includes a rounded outer shell-like top cover or outer housing 12 of molded plastic, such as polypropylene. The top cover 12 includes a slightly depressed region 14 in the upper portion thereof. An atomized or aerosolized liquid outlet opening 16 is provided within the region 14. A timing adjustment switch actuator 18 is located on the front of the top cover 12. This actuator 18 can be moved to the right and left to position a switch (to be described) in order to adjust the timing between successive actuations of the device 10.

FIG. 2 shows the bottom of the atomizing device 10. As can be seen, seen the device 10 is provided with a bottom cover 20 of molded plastic, which may be of the same material as the top cover 12. The bottom cover 20 has a pair of mounting elements 22 near one end which connect the bottom cover to interior components to be described. A hinge line 24 extends across the bottom cover 20 to allow a rearward region 20a thereof to bend downwardly away from the top cover 12 and open the device to permit access to its interior. A hole 26 is formed in the rearward region 20a of the bottom cover 20 enables one to observe the amount of liquid in a reservoir carried in the device without need to open the device. A latching mechanism 28 is formed at the end of the rearward region 20a opposite the hinge line 24. The latching mechanism interacts with locking recesses in the outer cover 12 for holding the rearward region closed. The latching mechanism 28 can be flexed to release the rearward region 20a of the bottom cover 20 from the top cover 12 so that the rearward extension can bend down and away from the top cover 12 along the hinge line 24 to open the device.

As shown in exploded array FIG. 3, there is provided inside the top cover 12, a chassis or main support 30 of molded plastic which extends in generally horizontal direction within the top cover 12. The main support 30 may be molded of the same type of plastic used in the top cover 10 and the bottom cover 20.

The main support 30 is generally in the form of a horizontal wall of the same outer configuration as that of the interior cross-section of the top cover 12; and the main support 30 extends within the top cover 12 to divide it into upper and lower chambers, as will be described. Also, the outer periphery of the main support 30 has a flange-like configuration, which allows the support to be locked into place within the top cover 12, as will also be described.

The main support 30 is formed near one end with two tubular support columns 32. These support columns telescope with and are affixed, for example by a snap fit, an adhesive or by welding, to the mounting elements 22 which project upwardly from the bottom cover 20. This supports the bottom cover in cantilever fashion so that it extends parallel to and below the main support 30 to provide a bottom wall for the atomizing device 10.

The main support 30 is also formed, on its upper surface, with an upwardly extending cylindrically shaped reservoir mounting wall 34 and a transition wall 35 which extends laterally inward from the top of the wall 34. The transition wall 35 supports a smaller diameter upwardly extending cylindrically shaped pump mounting wall 36. The cylindrical mounting walls 34 and 36 form a continuous passageway that extends through the main support 30. The reservoir mounting wall 34 is formed with bayonet type slots (not shown in FIG. 3) which are used to mount a liquid reservoir, as will be described. The pump mounting wall 36 is formed with an internal annular shelf 40 on which is supported a piezoelectric actuator and orifice plate pump assembly 42. An upper cylindrical retainer support wall 44 extends up from the transition wall 35 and surrounds the pump mounting wall 36. The retainer support wall 44 has at least one locking projection 46 extending out from its upper edge. This edge interlocks with a corresponding formation on a skirt 48 of a retainer 50. The retainer 50 has a center opening 52 with several resilient retainer elements or fingers 54 extending downwardly from the edge of the opening 52. When the piezoelectric actuator and orifice plate pump assembly 42 is positioned on the shelf 40, the retainer 50 is snapped onto the upper cylindrical support wall 42 so that its retainer fingers 54 press down on the piezoelectric actuator and orifice plate pump assembly 42 near its outer edge to hold it securely on the shelf 40.

The reservoir and pump mounting walls 34 and 36 open into a hollow wire chase 56 which extends radially outward therefrom. This wire chase contains wires (not shown) which extend from a printed circuit board assembly 58 to the piezoelectric actuator and orifice plate pump assembly 42, to supply alternating electrical fields or voltages produced by the printed circuit board assembly to opposite sides of the assembly.

The piezoelectric actuator and orifice plate pump assembly 42 comprises an annularly shaped piezoelectric element 60 across which extends an orifice plate 62. When high frequency alternating electric fields are applied to the element 60, as above described, it undergoes changes in certain of its physical dimensions; and this in turn causes the orifice plate 62 to vibrate up and down and atomize liquid which is supplied to the underside of the plate.

The support 30 is also formed on its upper side with corner supports 64. Corner support projections 66 are formed in the corner supports 64 and a printed circuit board 68 rests on these projections. The printed circuit board 68 supports the components of the printed circuit board assembly 58 which produce the high frequency alternating electric fields. Also formed on the upper side of the support 30 are a pair of resilient latching fingers 70 which extend over opposite edges of the printed circuit board 68 to hold it in place between the corner supports 64 and resting on the corner support projections 66. As can be seen, the printed circuit board 68 may be fitted in place simply by pressing it down between the corner supports 64 so that its edges bend the latching fingers 70 away. Then, when the printed circuit board is in place resting on the corner support projections 66, the latching fingers 70 can bend back to hold the printed circuit board in place. Should it be desired to remove the printed circuit board, the latching fingers 70 can be bent back to release the board and allow it to be removed.

A pair of battery contact holders 72 (only one of which is shown in FIG. 3) are integrally molded with, and extend down from, the lower surface of the main support 30. These holders are configured to press conductive leads against the ends of a standard AA battery held to the lower side of the main support 30. Battery lead openings 74 are also formed to extend through the main support 30 near the contact holders 72. These openings accommodate battery leads 76 (only one of which is shown in FIG. 3), which are held by the holders against the ends of a battery to connect the battery to the printed circuit board 68 and supply the printed circuit board with electrical power. As indicated above, the printed circuit board has mounted thereon electrical circuits and components which convert electrical power from the battery to alternating electrical fields which are applied via leads (not shown) to the piezoelectric element 60. The piezoelectric element in turn causes the orifice plate 62 to vibrate and atomize liquid which is supplied to the bottom of the orifice plate.

The circuits on the printed circuit board 68 include a switch 78 which is engaged by the switch actuator 18 on the front of the top cover 12 and which moves along a horizontal slot 12a in the top cover 12. Operation of the switch causes changes in the timing of actuation of the piezoelectric element 60.

Figure 4:
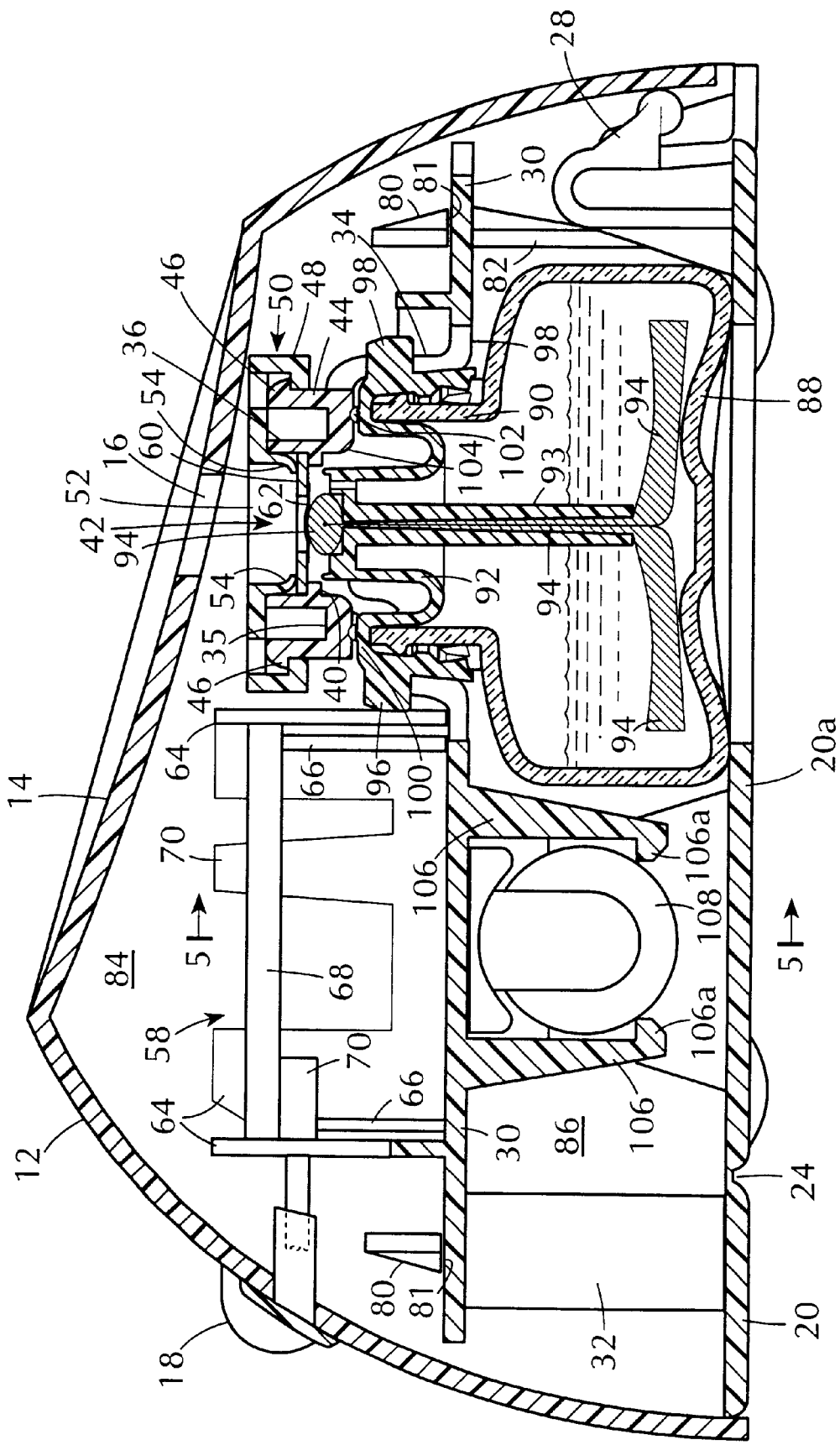
FIG. 4 is an elevational section view taken along line 4—4 of FIG. 2.

Referring now to FIG. 4, a plurality of spaced apart locating ribs 80 project inwardly of the top cover 12. These ribs have lower abutments 81 against which the outer edges of the main support 30 rest to hold the main support in a horizontal position about half way between the top and bottom of the cover. Thus, the interior of the cover is divided by the main support 30 into upper and lower internal chambers 84 and 86. There are also formed in the cover 12, just under some of the locating ribs 80, locking ribs 82. These locking ribs do not project outwardly as far as the locating ribs 80 so that the flangelike periphery of the main support 30 may be pushed over them. Nevertheless the locking ribs 82 do hold the support 30 in place against the abutments 81.

As can also be seen in FIG. 4, there is provided a removable liquid reservoir 88 having a neck 90 over which a combination plug and wickholder 92 is firmly affixed in a sealing and non-rotating relationship. A looped over wick 94 extends from within the liquid reservoir 88 and up through a center tube 93 in the combination plug and wickholder 92 to a location just above its upper surface. The wick 94 transfers liquid from within the reservoir 88 to the bottom of the orifice plate 62 of the pump assembly 42. As can be seen in FIG. 4, the looped over portion of the wick 94 is positioned to deliver liquid to the orifice plate without appreciably damping its vibrations. It is important that the wick not press against the orifice plate with any appreciable force because this would interfere with the vibrational characteristics of the plate and may reduce or even eliminate its effectiveness in atomizing liquid which it transfers from the reservoir to the plate. A preferred construction of the reservoir 88 and the plug and wickholder 92 is shown and described in copending application Ser. No. 09/630882 filed Aug. 2, 2000 and assigned to the assignee of the subject application.

The combination plug and wickholder 92, in some aspects of the invention, may be integral with and may form part of the liquid reservoir 88. In any event, a pair of mounting lugs 96 extend laterally outwardly from the reservoir or from the plug and wickholder to engage corresponding bayonet type slots 98 in the reservoir mounting formation 36. This permits the liquid reservoir 88 to be easily inserted into the atomizer assembly and then turned to become locked in position in the lower chamber 86 as shown in FIG. 4, with the wick 94 positioned to deliver liquid to the orifice plate 62. Also, by reversely turning the reservoir 88, it can be released from the slots 98 for replacement with a new reservoir.

The slots 98 are slightly slanted in an upward direction so that when the reservoir is turned, the upwardly facing bottom surfaces of the slots 98 cause the lugs 96 to be cammed to bring an upper surface 100 of the plug and wickholder 92 into sealing contact at 102 with a lower surface 104 of the transition 35 between the reservoir and pump assembly walls 34 and 36.

The main support 30 is also formed with a pair of battery holding elements 106 which extend down into the lower internal chamber 86. The elements 106 are resiliently bendable and they are provided at their lower ends with catches 106a to hold a battery 108 in a manner which allows it to be removed and replaced.

Turning now to FIG. 5, it will be seen that the battery 108, when mounted in the atomizing device, fits between the contact holders 72 which hold the battery leads 76 against the ends of the battery. These leads extend up through openings 77 in the main support 30 and connect to the printed circuit board 68. The leads 76 are mounted on the printed circuit board 68 with the other elements that make up the printed circuit board assembly 58 (FIG. 3). When the printed circuit board assembly is mounted onto the main support 30, the leads 76 are passed through the openings 77 and into position against the contact holders 72.

In operation of the device, the battery 108 supplies electrical power via the leads 76 to electrical circuits on the printed circuit board assembly 58. These circuits produce the high frequency alternating voltages which are supplied to the upper and lower sides of the piezoelectric actuator 60. Any oscillating circuit capable of producing alternating voltages is adequate for the purposes of this invention; but an especially desirable circuit is described in copending U.S. application Ser. No. 09/519,560, filed on Mar. 6, 2000, now U.S. Pat. No. 6,296,196 and assigned to the assignee of the present invention. The actuator 60, in response to these alternating voltages, expands and contracts and causes the orifice plate 62 to vibrate up and down as explained above. Meanwhile, the wick 94, by capillary action, draws liquid from the reservoir 88 up to the bottom of the orifice plate 62. The up and down vibrations of the orifice plate pump this liquid through minute orifices which are formed in the plate; and these vibrations cause the liquid to be ejected from the upper surface of the plate in the form of aerosolized liquid particles. These liquid particles exit from the device through the opening 16 in the top cover 12.

It is important that the wick 94 be very precisely positioned relative to the orifice plate 62. The wick must be positioned close enough to the orifice plate that it will be able to feed liquid to be atomized to the plate. On the other hand, the wick 94 must not press appreciably against the plate 62, otherwise it will damp the plate's vibration and adversely affect or even prevent atomization of the liquid. The wick 94, however, is not a part of the atomizing device itself but instead it is a part of the replaceable refill container 88. Thus, in order to position the wick properly with respect to the orifice plate 62, the wick must be accurately positioned in the refill container 88 and the refill container must be mounted very precisely in the main support 30.

It will be appreciated that the main support 30, which is molded as a single piece, provides an upwardly facing locating surface on the shelf 40 and a downwardly facing locating surface 104 at the transition between the reservoir and pump assembly mounting walls 34 and 36. Accordingly, the locating surfaces 34 and 36 are displaced from each other by a precise amount and are not subject to the dimensional variations that would be encountered if these locating surfaces had been formed on separate members. This precise displacement of the locating surfaces 34 and 36 ensures that the reservoir 88 and its wick 94 are located such that the wick 94 can deliver liquid to be atomized to the orifice plate without pressing appreciably against the plate and damping its vibrations.

It will also be appreciated that the main support 30 may be formed easily as a simple molded object even though it mounts the pump assembly 42, the printed circuit board assembly 58, the liquid reservoir 88 and the battery 108. Furthermore, each of these elements can easily be snapped or turned into place on the main support 30 and held in precise locations thereon. Also, the more permanent components, namely the pump assembly 42 and the printed circuit board assembly 58, are located in the upper region 84 s inside the top cover 12, while the replaceable components, namely, the liquid reservoir 88 and the battery 108, are located in the lower region 86 inside the top cover 12.

The atomizer device of this invention is easily assembled by first telescoping the mounting elements 22 on the bottom cover 20 into the tubular support columns 32 of the main support 30 and fixing them in place by any convenient means, such as by a snap fit, an adhesive or by welding, for example. Then the components to be mounted on the main support 30 are snapped into place. Thus, the printed circuit board assembly 58 is positioned on the supports 66 and held in place between the latching fingers 70.

The pump assembly 42 is placed on the shelf 40, with the wires that extend between the circuit board assembly 58 and pump assembly 42 passing through the wire chase 56. Thereafter, the pump retainer 50 is snapped over the outer cylindrical wall 44 so that the resilient fingers 54 press the pump assembly 42 down against the wall 40. The main support 30, with these elements mounted thereon, can then be snapped into place inside the top cover 12 by pressing the flange-like outer periphery of the main support up against the ribs 80, whereby the main support is held in place by the lower ribs 82 inside the top cover 12. The switch actuator 18 can then be fitted to extend in through the slot 12a in the top cover 12 to engage the switch 78 on the printed circuit board assembly 58. The battery 108 can be snapped into place between the elements 106 on the main support 30 and the liquid reservoir may be mounted in place by fitting the projecting lugs 96 thereon into the slots 98 which are formed in the reservoir mounting wall 34 of the main support. This accurately positions the wick 94 which is carried by the reservoir so that it can deliver liquid to be atomized to the orifice plate 62 without pressing appreciably against the plate and damping its vibrations. Thereafter the bottom cover 20 may be closed and latched in place as shown in FIG. 4 for operation of the device. During operation, the contents of the liquid reservoir can be viewed through the hole 26 located in the bottom cover 20. Wherever the liquid reservoir 88 or the battery 108 needs to be replaced, this may be done simply by operating the latch 28 and bending the bottom cover extension 20a downwardly to allow the battery or the liquid reservoir to be removed and a new battery or liquid reservoir inserted into place as described above.

It should be understood that the main support 30 may be formed with a single cylindrical wall instead of the two walls 34 and 36; and in such case, the internal annular shelf 40 as well and the bayonet slots 98, could be located along the inner surface of this wall. Also, in place of the bayonet type slots, other releasable formations may be provided on the cylindrical wall or at some other location on the main support, to hold the liquid reservoir in place.

What is claimed is:

1. In a liquid atomizer device, the combination of:
   a hollow shell-like top cover formed with an upper atomized liquid ejection opening; and
   a generally horizontal integrally molded support mounted inside the top cover and dividing the interior of said top cover into upper and lower regions, said support being formed with a passageway communicating between said regions, said support also being formed, on its upper and lower sides, respectively, with upwardly and a downwardly facing locating surfaces which surround said passageway for locating a vibratory orifice plate on the upper side of said support and for locating a replaceable liquid reservoir on the lower side of said support, said support further being formed with an upwardly facing camming surface below said downwardly facing surface for holding a liquid reservoir up against said downwardly facing locating surface for precise positioning of a liquid reservoir relative to an orifice plate mounted on said upwardly facing locating surface.

2. A liquid atomizer device according to claim 1, wherein said support is formed on its upper surface with mounting elements for holding electrical circuits which drive an orifice plate vibrator.

3. A liquid atomizer device according to claim 1, wherein said support is formed on its lower surface with holding elements for holding a battery in said lower region.

4. A liquid atomizer device according to claim 1, wherein said camming surface is formed as a bottom surface of a bayonet type slot formed in said support.

5. A liquid atomizer device according to claim 1, wherein said upwardly and downwardly facing locating surfaces are formed in the same unitary molded structure.

6. A liquid atomizer device according to claim 1, wherein said support further includes resilient fingers arranged to hold a vibratory orifice plate in a fixed position supported on said upwardly facing locating surface.

7. A liquid atomizer device according to claim 1, wherein said device further includes a pump assembly comprising an annular piezoelectric actuator having a perforated plate affixed thereto and extending thereacross, said pump assembly being supported by said upwardly facing locating surface, and an electrical oscillator circuit connected to supply high frequency alternating voltages across opposite surfaces of said piezoelectric actuator.

8. A liquid atomizer device according to claim 7, wherein said support further includes resilient fingers arranged to hold a vibratory orifice plate in a fixed position supported on said upwardly facing surface and wherein said resilient fingers press said actuator against said upwardly facing locating surface.

9. A liquid atomizer device according to claim 7, wherein a switch actuator extends through a slot in said top cover to engage an operating switch on said electrical oscillator circuit inside said top cover.

10. A liquid atomizer device according to claim 7, wherein said perforated plate is soldered to said piezoelectric actuator.

11. In a liquid atomizer device, the combination of:
    a hollow shell-like top cover formed with an upper atomized liquid ejection opening; and
    a generally horizontally extending main support dividing the interior of said top cover into upper and lower regions, said support being formed with a passageway communicating between said regions, said main support also being formed, on its upper and lower sides, respectively, with mounting formations for mounting an orifice plate in an upper region of said passageway and removably mounting a liquid reservoir in a lower region of said passageway below said orifice plate, said main support also being formed on an upper side thereof with circuit mounting elements for mounting a drive circuit which causes an orifice plate to vibrate and further being formed on a lower side thereof with battery mounting elements, whereby access is easily available to replace a battery or a liquid reservoir without disturbing such vibratory orifice plate and drive circuit.

12. A liquid atomizer device according to claim 11, wherein a bottom cover extends across and closes the bottom of said top cover.

13. A liquid atomizer device according to claim 12, wherein said bottom cover is openable from said top cover to provide access to a removable battery and to a removable liquid reservoir mounted on said lower side of said main support.

14. A liquid atomizer device according to claim 13, wherein said bottom cover is attached by a spacer to extend parallel to and spaced apart from said main support to form a region for containing a removable liquid reservoir and a removable battery.

15. A liquid atomizer device according to claim 13, wherein said spacer is located near one end of said bottom cover and wherein a hinge configuration extends across said bottom cover close to said spacer to permit the major portion of said bottom cover to bend down to provide access to a removable battery and to a removable liquid reservoir mounted on the lower side of said main support.

16. A liquid atomizer device according to claim 15, wherein a releasable latch is provided at the end of said bottom cover opposite said spacer to hold said end releasably to said top cover.

17. A liquid atomizer device according to claim 13, wherein said bottom cover is provided with a hole to permit observation of the contents of a liquid reservoir being held by said main support.

18. A retainer assembly for a piezoelectric atomizing pump of the type which comprises an annular piezoelectric element having a center opening and an orifice plate fixed to said piezoelectric element and extending across said opening, said retainer assembly comprising:
   a vertically extending cylindrical wall within which a piezoelectric atomizing pump assembly may fit, said cylindrical wall being formed with an inwardly extending shelf for supporting a piezoelectric pump assembly;
   a retainer having a horizontally extending annular wall which rests on an end of said cylindrical wall above said shelf, said retainer being removably secured to said tubular support; and
   a plurality of resilient retainer elements extending from an inner edge of said annular wall and down inside said tubular support to press on said piezoelectric pump assembly resting on said shelf.

19. A retainer assembly according to claim 18, wherein said retainer is molded from flexible plastic material and has a skirt extending down from said annular wall, said skirt extending over an outer cylindrical surface and releasable interlocking formations arranged on said skirt and on said outer cylindrical surface for releasably holding said retainer to said cylindrical wall.

20. A retainer assembly according to claim 19, wherein said cylindrical outer surface is formed on an outer wall which surrounds said cylindrical wall.

21. A retainer assembly according to claim 18, wherein said cylindrical wall is integrally molded with a liquid reservoir retaining formation which holds a liquid reservoir in a fixed location relative to said inwardly extending shelf.

22. An easily assemblable self contained liquid atomizer assembly comprising:
   a hollow molded top cover having spaced apart support projections which extend inwardly from an inner surface thereof and retainer formations located below said support formations, said top cover also being formed with an upper atomized liquid ejection opening;
   a unitary molded internal support having a generally horizontal flange-like surface which rests against said support projections and which can be snapped into and held in place within said top cover by said retainer formations,
   said internal support being formed with a passage in alignment with said ejection opening,
   the upper side of said internal support also being formed with upwardly facing support surfaces on which a printed circuit board may rest and on which a piezoelectric pump assembly, positioned over said passage, may rest, said upper side also being provided with snap elements which permit such printed circuit board and pump assembly to be snapped into and held in place on the upper side of said internal support,
   the lower side of said internal support being formed with releasable retainer elements for releasably holding a liquid reservoir under said passage and for releasably holding a battery adjacent said reservoir,
   said internal support being formed with openings for accommodating wires which extend from a battery to a printed circuit board held by said support and openings for accommodating wires which extend between said printed circuit board and a piezoelectric pump assembly held by said support.

23. In a liquid atomizer device, the combination of:
   a hollow shell-like top cover formed with an upper atomized liquid ejection opening; and
   a generally horizontal integrally molded support dividing the interior of said top cover into upper and lower regions, said support being formed with a passageway communicating between said regions, said support also being formed, on its upper and lower sides, respectively, with upwardly and a downwardly facing locating surfaces which surround said passageway for locating a vibratory orifice plate on the upper side of said support and for locating a replaceable liquid reservoir on the lower side of said support, said support further being formed with an upwardly facing camming surface below said downwardly facing surface for holding a liquid reservoir up against said downwardly facing locating surface for precise positioning of a liquid reservoir relative to an orifice plate mounted on said upwardly facing locating surface.

24. A liquid atomizer device according to claim 23, wherein said support is formed on its upper surface with mounting elements for holding electrical circuits which generate alternating electrical fields for driving an orifice plate vibrator.

25. A liquid atomizer device according to claim 23, wherein said support is formed on its lower surface with holding elements for holding a battery in said lower region.

26. In a liquid atomizer device, the combination of:
   a hollow shell-like top cover formed with an upper atomized liquid ejection opening; and a generally horizontal main support dividing the interior of said top cover into upper and lower regions, said support being formed with a passageway communicating between said regions, said support also being formed, on its upper and lower sides, respectively, with mounting formations for mounting an orifice plate above said passageway and removably mounting a liquid reservoir below said passageway, said main support also being formed on its upper side with circuit mounting elements for mounting a drive circuit which causes an orifice plate to vibrate and further being formed on its lower side with battery mounting elements, whereby access is easily available to replace a battery or a liquid reservoir without disturbing said vibratory orifice plate and drive circuit.

27. A liquid atomizer device according to claim 26, wherein a bottom cover is mounted to said main support to extend below said main support and cover the bottom of said top cover.

28. A liquid atomizer according to claim 27, wherein said bottom cover is connected by tubular spacer members to said main support.

29. A liquid atomizer according to claim 27, wherein said bottom cover is hinged so that a portion thereof can open from said top cover to provide access to the lower region of the interior of said top cover.

30. A liquid atomizer according to claim 29, wherein said portion of said bottom cover is provided with a latch which releasably holds said portion to said top cover.

31. A liquid atomizer according to claim 26, wherein said mounting formations include at least one cylindrical wall extending up from said main support and being provided with at least one slot for mounting a liquid reservoir and an internal shelf for mounting said orifice plate.

* * * * *